United States Patent [19]
Kohen et al.

[11] Patent Number: 6,108,570
[45] Date of Patent: *Aug. 22, 2000

[54] NON-INVASIVE DEVICE AND METHOD FOR QUANTITATIVE DETERMINATION OF OXIDANTS AND/OR ANTIOXIDANTS IN THE SKIN

[75] Inventors: Ron Kohen; David Fanberstein, both of Jerusalem; Oren Tirosh, Holon, all of Israel

[73] Assignee: Yissum Research Development Company of the Hebrew University of Jerusalem, Israel

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/817,222
[22] PCT Filed: Oct. 10, 1995
[86] PCT No.: PCT/US95/13550
§ 371 Date: Jun. 23, 1997
§ 102(e) Date: Jun. 23, 1997
[87] PCT Pub. No.: WO96/13193
PCT Pub. Date: May 9, 1996

[51] Int. Cl.[7] ........................................................ A61B 5/05
[52] U.S. Cl. ............................................. 600/345; 600/354
[58] Field of Search ..................................... 600/345–348, 600/354, 363, 357, 365, 382, 309, 386–390, 393, 395–397

[56] References Cited

U.S. PATENT DOCUMENTS

| | | |
|---|---|---|
| 4,317,705 | 3/1982 | Hamada et al. . |
| 4,396,687 | 8/1983 | Kummer et al. . |
| 5,108,564 | 4/1992 | Szuminsky et al. . |
| 5,161,532 | 11/1992 | Joseph ...................................... 600/345 |
| 5,342,490 | 8/1994 | Lever et al. . |
| 5,771,890 | 6/1998 | Tamada ................................... 600/345 |

*Primary Examiner*—Cary O'Connor
*Assistant Examiner*—Ryan Carter
*Attorney, Agent, or Firm*—Kohn & Associates

[57] ABSTRACT

A non-invasive device for the quantitative determination of the level of oxidants and/or antioxidants in the skin of a subject includes a reference electrode and a working electrode which are connected to an electrical voltage measuring device; and a test solution container which is open at a bottom side thereof and which is placed on the skin of the subject and is sealingly but releasably affixed to the skin, is filled with a test solution, and which permits contact between the test solution and the skin. The test solution container further includes a top opening through which the electrodes are immersed in the test solution.

29 Claims, 2 Drawing Sheets

NON-INVASIVE DEVICE AND METHOD FOR QUANTITATIVE DETERMINATION OF OXIDANTS AND/OR ANTIOXIDANTS IN THE SKIN

FIELD OF THE INVENTION

The invention relates to a non-invasive device and method for the quantitative determination of the level of oxidants and/or antioxidants in the skin.

BACKGROUND OF THE INVENTION

In the last decade many details have been clarified which contribute to understanding the role of oxygen free radicals and other oxygen metabolites in biology and medicine. Reactive oxygen species have been incriminated as deleterious species which are responsible for the biological damage induced by oxidative stress in many clinical cases, and today these metabolites are considered to be responsible for the oxygen toxicity in mammals, bacteria and plants. Humans are exposed to many types of oxygen metabolites from both endogenous and exogenous sources. During the reduction in stages of the oxygen molecule in the mitochondria for energy generation, active oxygen species are produced. These metabolites, which include the superoxide radical ($O_2^{-\bullet}$), hydrogen peroxide ($H_2O_2$) and the hydroxyl radical ($OH^\bullet$), can leak to the immediate surroundings and may cause biological damage. Other internal sources for reactive oxygen species are enzymes which produce these metabolites as a result of their catalytic activity. The production of oxygen reactive metabolites can also occur in many other systems. Phagocytes, for example, are known for their ability to produce the superoxide radical and other reactive species. Other species also participate in the defense mechanism against invaders. This process, although necessary, can lead to biological damage in the surrounding area.

Exposure of humans to free radicals is not limited to the endogenous oxygen free radicals, but also includes exogenous sources. Various chemicals in agricultural use can serve as free radical generation systems, as in the case of the herbicide Paraquat. Other chemicals (aloxan, isouramil, cigarette smoke, air pollutants, carcinogenic and mutagenic compounds and many drugs) can generate oxygen free metabolites and cause biological damage. Free radicals have been shown to play an important role in the initiation and pathogenesis of, inter alia, inflammations, autoimmune diseases, brain degenerative diseases (Parkinson, Wilson, epilepsy), and eye diseases (cataract and retinopathy). These reactive species have also been demonstrated to be involved in ischemic and post-ischemic damage to the heart, brain and gastrointestinal tract. Recently it has been suggested that oxygen free radicals take part in cancer, aging and aging-related diseases.

Antioxidants

Exposure of the cells to continuous efflux of oxygen free radicals and reactive species led to the adaptation of the cells to live in an aerobic atmosphere. This adaptation process included the development of several lines of defense (antioxidants) against the damage induced by these metabolites. The broad definition of an antioxidant includes compounds which can cope with oxidative stress in various mechanisms. These mechanisms include: compounds which donate hydrogen to the damaged target, compounds which can scavenge free radicals, compounds which can bind the oxidants and remove them from the target, compounds which can convert reactive species to nonreactive metabolites, and reducing compounds which can react with oxidants. The various antioxidants may be classified into two main groups: the enzymatic group of antioxidants and the low molecular weight antioxidants (LMWA). The antioxidant enzymes include the enzymes superoxide dismutase, catalase and peroxidase. The LMWA include compounds which are not synthesized by humans but are present in the diet, such as ascorbic acid (vitamin C), tocopherol (vitamin E) and compounds which can be synthesized by humans such as glutathione (GSH), carnosine (an antioxidant present in the brain and muscle), uric acid and others. Most of the compounds in this group are reducing agents which can react with the oxidants.

Lipid Peroxidation Process

Among the various mechanisms that explain the oxidative damage of various biological systems, the lipid peroxidation process is of major importance. The occurrence of lipid peroxidation in biological membranes causes impairment of membrane functioning, decreased fluidity, inactivation of membrane-bound receptors and enzymes, and increased non-specific permeability to ions such as Ca(II). Peroxidation is initiated by the attack of any chemical species that has sufficient reactivity to abstract a hydrogen atom from a methylene carbon in the side chain. The hydrogen atom is a free radical and its removal leaves behind an unpaired electron on the carbon atom to which it was originally attached. The resulting carbon centered radical ($L^\bullet$) can have several fates, but the most likely one in aerobic cells is that it will undergo molecular rearrangement, followed by a reaction with molecular oxygen to yield a peroxy radical ($ROO^\bullet$). Peroxy radicals can combine with each other or they can attack membrane proteins, but they are also capable of abstracting hydrogen from adjacent fatty acid side chains in a membrane and in so doing propagate the chain reaction of lipid peroxidation. The result of this hydrogen atom abstraction is the production of lipid hydroperoxide (ROOH).

Evaluation of Lipid Peroxidation

Evaluation of the lipid peroxidation status in food products is important for the estimation of shelf life (for food products) and in biological systems for assessing the clinical condition of the organism. It has been shown that an increase in the oxidation of lipids correlates with the aging process and with pathological events in the cell. The measurement of the lipid peroxidation process and products in human materials is probably the evidence most frequently quoted in support of the involvment of free radicals reactions in tissue damage by disease. Oxidation of lipids can be measured at different stages, including (1) measurement of losses of unsaturated fatty acid; (2) measurement of primary peroxidation products; and (3) measurement of secondary carbonyls and hydrocarbon gases. Search of the scientific literature reveals that there is no method to evaluate lipid peroxidation of animal skin by a non-invasive procedure.

Evaluation of Antioxidant Activity

One of the major problems in this field of free radicals and antioxidants is the evaluation of the ability of a certain biological tissue or fluid (blood, CSF, saliva, sperm, etc.) to cope with the oxidative stress and to prevent the biological damage. The existing methods are based on the measurement and quantification of a specific compound or several compounds in body tissue or the determination of the concentration of a compound or several compounds following exposure of the tissue or the animal to oxidative stress. These methods are insufficient as they give only partial information on the tissue antioxidant status.

Antioxidant Activity of the Skin

The epidermis provides the first line of defense against oxidative stress and reactive oxygen species. It has been shown that the surface of the skin is equipped with a defending system which copes with the oxidative stress. The sources of the oxidative stress may be internal (such as infiltration of neutrophils and macrophages into inflamed skin or ischemic process) or external (inonizing radiation; UV light; photochemical reaction products such as superoxide radicals, hydrogen peroxide, hydroxyl radicals; products of the lipid peroxidation process or physical burns). The variety of the antioxidant compounds in intact skin have never been studied in detailed. Non-invasive methods for evaluating the LMWA were not available.

SUMMARY OF THE INVENTION

The invention relates to a non-invasive device for the quantitative determination of the level of oxidants and/or antioxidants in the skin of a subject comprising a pair of a reference electrode and a working electrode which are connected to electrical voltage measuring means; a test solution container which is open at the bottom side thereof which is placed on the skin of said subject and is releasably but sealingly affixed to the skin by suitable means, filled with a test solution, which solution containing reagent which are capable of being oxidized or reduced by oxidants or antioxidants, respectively, and permitting contact between said test solution and the skin, and is open at the top side thereof through which said electrodes are immersed in said test solution.

The invention also relates to a non-invasive method for the quantitative determination of the level of oxidants or antioxidants in the skin of a subject comprising the steps of sealingly affixing to the skin of the subject a test solution container which is open at the side thereof which is placed on the skin of said subject in a releasable manner by suitable means; filling said container with a suitable test solution, said test solution containing reagents which are capable of being oxidized or reduced by oxidants or antioxidants present in the skin of said subject, respectively; immersing a pair of a reference electrode and a working electrode, which are connected to electrical voltage measuring means, in said test solution; and measuring the electrical voltage of said test solution at appropriate time points; whereby the concentration of the oxidants or antioxidants in the skin of said subject is determined from the change in the electric potential of said test solution.

DESCRIPTION OF THE INVENTION

Figure 1:
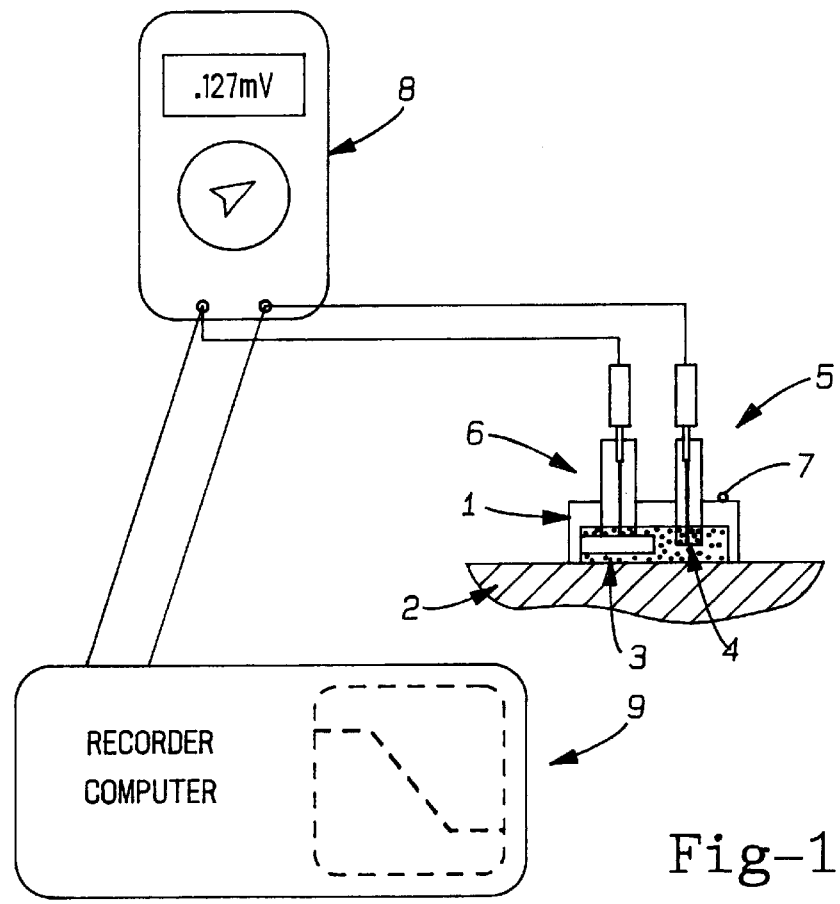
FIG. 1: a schematic illustration of a device according to the invention.

The present invention relates to a non-invasive device for the quantitative determination of the level of oxidants and/or antioxidants in the skin of a subject comprising a pair of a reference electrode and a working electrode which are connected to electrical voltage measuring means; a test solution container which is open at the bottom side thereof which is placed on the skin of said subject and is releasably but sealingly affixed to the skin by suitable means, filled with said test solution and permitting contact between a test solution and the skin, said test solution containing reagent which are capable of being oxidized or reduced by oxidants or antioxidants, respectively, and is open at the top side thereof through which said electrodes are immersed in said test solution.

The device according to the invention may further comprising means for accommodating said electrodes and holding the same within said test solution.

The reference electrode is preferably a Ag/AgCl electrode or a calomel electrode and said working electrode is preferably a glossy carbon, gold or platinum electrode.

The container is preferably an open-sided hollow cylinder and is preferably made from plastics material, such as, e.g. Plexyglass®.

The means for affixing the test solution container to the skin of the subject are any physiologically compatible affixing means, such as e.g., silicone glue.

The test solution for the determination of oxidants in the skin is preferably an aqueous iodide or iodide-iodine solution, for example, an aqueous KI or $KI/I_2$ solution.

The test solution for the determination of the level of antioxidants is can be an aqueous iodine solution, an acidic aqueous Fe(III) salt solution, for example an aqueous $FeCl_3$ solution, $pH \leq 2$, or an aqueous solution containing chelated Fe(III), for example an aqueous ADP-Fe(III) solution.

The device according to the invention is preferably further equipped with means for recording the measured electrical voltage values.

The invention also provides a non-invasive method for the quantitative determination of the level of oxidants or antioxidants in the skin of a subject, comprising the steps of: sealingly affixing to the skin of the subject a test solution container which is open at the side thereof which is placed on the skin of said subject in a releasable manner by suitable means; filling said container with a suitable test solution, said test solution containing reagents which are capable of being oxidized or reduced by oxidants or antioxidants present in the skin of said subject, respectively; immersing a pair of a reference electrode and a working electrode, which are connected to electrical voltage measuring means, in said test solution; and measuring the electrical voltage of said test solution at appropriate time points; whereby the concentration of the oxidants or antioxidants in the skin of said subject is determined from the change in the electric potential of said test solution.

Based on the fact that most of the LMWA are reducing agents (glutathione, ascorbic acid, tocopherols, carnosine, phenols and other small molecules), the inventors have developed a new technique for measuring the total antioxidant capacity of a biological fluid or biological tissue homogenate. This new technique is based on measurements of the redox potential of redox solutions prior and following exposure to the oxidative stress. It has been previously shown [Kohen, R., et al., Free Rad. Res. Comms. 17(4): 239–248 (1992); Kohen, R., et al., Ex[erimental Gerontology 27:161–168 (1992)] that measurement of the oxidation potential of biological fluids by cyclic voltammetry is in correlation with the antioxidant activity. In the cyclic voltammetry technique increasing voltage is applied to the electrodes, and electrons are transferred from a reducing agent present in the solution to the strongly positively charged electrodes. It is essential that the tested sample be in the form of liquid. This technique has now been further developed and modified so that measurement of the redox potential (and not the oxidation potential) can indicate the reducing capacity of the tested tissue. When measuring redox potential, no voltage is applied to the electrodes. The presence of an electrochemical couple in the tested sample, or a solution in contact therewith, generates changes in voltage which are measured and recorded. The recorded redox potential and the Nernest equation are used to find the concentration of the reducing equivalents in the tested biological sample, as will be shown below in more detail. Measurement of the redox potential enables to evaluate in a non-invasive manner the reducing power of skin which correlates with its antioxidant activity.

The present device and method enable, for example, the evaluation of the lipid hydroperoxide (a major primary metabolite in the lipid peroxidation process) in a non-invasive manner. This quantification is based on an in-vitro chemical reaction, a technique used in the food industry for evaluating the peroxide number of unsaturated fatty acid (see below).

Redox potential can be easily measured by the use of voltmeter. The value obtained is constant and characterized for each electrochemical solution as long as no change occurred in the solution's characteristics (temperature, light, pH, ingredients interactions, concentration, etc). A change in any one of these parameters causes a change in the potential recorded.

A solution which contains only the reduced and oxidized forms of the same compounds can be defined as an electrochemical cell. Such a cell can be determined by the Nernest equation:

$$E = E^O + RT/nF \ln [\text{OXIDANT/REDUCTANT}]$$

where:

E=potential recorded $E^O$=standard potential (literature)

R=Gases constant (8.31 J/mole)

T=temperature (Kalvin) (room temperature –298 K)

n=number of electrons participating in the redox reaction

F=Faraday constant (96000 cb).

In each measurement of a given solution all the parameters are constant except the potential (E) and the concentration of the oxidized species [OXIDANT] and the reduced species [REDUCTANT]. If two of these values are known, the third value can be determined.

The use of a solution with a known concentration of the oxidant or the reductant species of a certain compound in a system which contains a reducing agent or an oxidizing agent respectively, will result in the formation of a reduced form of the same compound (result of the reduction of the oxidized form) or an oxidant of the same compound, (result of the oxidation of the reduced form) respectively. An electrochemical couple will then be formed and the potential (E) of the solution can be measured. If the concentration of the oxidized compound which was introduced is high enough, the change in its concentration can be neglected and the concentration of the reduced form can be determined from the Nernest equation. The concentration of the reduced form of the compound is in correlation with the reducing activity of the test sample. A similar calculation can be made for oxidation processes.

In the past, in order to evaluate the redox or the oxidation potential of skin, one had to remove the skin, homogenate it and then measure the potential. In the present, non-invasive method, the solution is placed in a well on the surface of the skin. Following a predetermined period or periods of time, the potential of the solution is recorded and by the Nernest equation, knowing the initial concentration of the solution employed, the concentration of the other form produced from the interaction of the solution with ingredients present on the surface of the skin can be calculated. One embodiment of a device according to the invention is schematically illustrated in FIG. 1. The bottom open side (3) of a test solution container (1), is releasably but sealingly affixed to the skin of a subject (2) by suitable physiologically compatible means (not shown). The container then is filled with a suitable test solution (4). A pair of a reference electrode (5) and working electrode (6) are introduced into the container (1) through the top side (7) thereof and preferably maintained immersed in the test solution by suitable means (not shown). The electrodes are connected to voltage measuring means (8), which may optionally be equipped with data recording means (9). The changes in the potential of the solution are recorded at any desired time points. After test is completed, the electrodes are disconnected, removed from the test solution container, which, in turn, is released from the skin of the subject.

The method of the present invention may be of particular importance for evaluating damage to skin of a subject following exposure to UV or radioactive radiation, burns, inflammation or ischemia by determining decrease of level of antioxidants or increase in level of oxidants in the skin of the subject. This will become apparent from the following examples.

EXAMPLES

1. General Method (a) Evaluation of Oxidant Status of Skin (Quantitation of Skin Peroxide Number)

Peroxide number of oxidized lipid (lipid hydroperoxide) is carried out in vitro by measuring the concentration of iodine ($I_2$) from iodide ($I^-$) and lipid hydroperoxide (Reaction 1):

ROOH (lipid hydroperoxide)+$I^-$ - - - $I_2$     [1]

Production of iodine is correlated to the ROOH in the tested solution and serves as an indicator for the peroxidation process.

A solution of $I^-$ or a solution of $KI/I_2$ of a known concentration is introduced into the well (FIG. 1). The potential of the solution is recorded at 10 min intervals for 60 min. If the surface of the skin (stratum corneum) or the epidermis contain a lipid hydroperoxide adduct, iodine is produced. The presence of both species creates an electrochemical cell in which the potential can be easily detected. The concentration of iodide is known. The changes in the potential (E) are in correlation with the production of iodine solution (the concentration of the lipid hydroperoxide molecules) in the skin (Reaction 2).

ROOH in the skin+$I^-$ - - - $I_2$     [2]

Procedure

In 100 ml of double distilled water, 3 g of KI and 1 g of iodine were dissolved. The redox potential of this solution was found to be –360 mV. The potential was recorded using a glossy carbon electrode as a working electrode and Ag/AgCl as a reference electrode. The solution and the electrodes were placed on the skin as shown in FIG. 1. The ring (well) was made from plexyglass and was affixed to the skin using silicone glue. The electrodes were connected to a digital voltmeter.

(b) Evaluation of Antioxidant Status of Skin

Antioxidants as described in the background section can be classified into two major groups: the enzymes and the low molecular weight antioxidants. In order to evaluate the antioxidant activity of skin which results from these low molecular weight compounds, a solution of oxidized species was introduced to the well of the device, placed on the skin. Reducing equivalents in the skin (low molecular weight antioxidants) react with the oxidized species in the solution to produce the reduced forms of these species. The result of the presence in the solution of both reduced and oxidized forms is an electrochemical cell with a potential (E) that can be easily recorded. Since the concentration of the oxidized solution is known and the potential (E) is known, the concentration of the reduced species in the tested solution (Nernest equation) can be calculated. The concentration of the reduced species correlates to the reducing equivalents in the surface of the area of the skin examined. The reducing equivalents are in correlation with the antioxidant activity on the skin (the reducing equivalents are low molecular weight compounds). Therefore, measurement of the potential (E) of the tested solution can be used as an indication of the antioxidant capacity of the skin.

Procedure

A solution of Fe(III) ($FeCl_3$) (0.2 M, pH$\leq$2) was found to be stable and was placed in the well of the device, affixed to the skin. The initial potential of the solution was found to be −600 mV (Reaction 3). (Alternatively, a solution of iodine was placed in the well and the potential resulting from the production of iodide was recorded—Reaction 4). The potential of the solution was recorded at 10 min intervals for 60 minutes. The potential was recorded using a glossy carbon electrode as working electrode and Ag/AgCl as a reference electrode. The solution and the electrodes were applied as shown in FIG. 1. The ring (well) was made from Plexyglass® and was affixed to the skin using silicone glue. The electrodes were connected to a digital voltmeter.

Fe(III)+reducing equivalents in the skin - - - Fe(II)+oxidized equivalents in the skin (antioxidants) Fe(III)/Fe(II) is an electrochemical couple. [3]

$I_2$+reducing equivalents in the skin - - - $I^-$+oxidized equivalents in the skin (antioxidants) $I^-/I_2$ is an electrochemical couple. [4]

Figure 2:
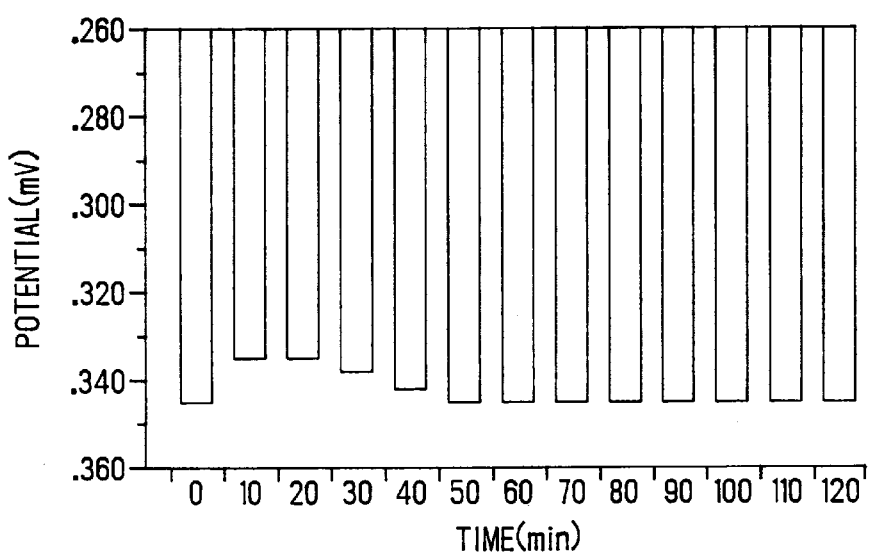
FIG. 2: The changes in potential (E) of a solution of $I^-/I_2$ with time on the skin of young rats.
Figure 3:
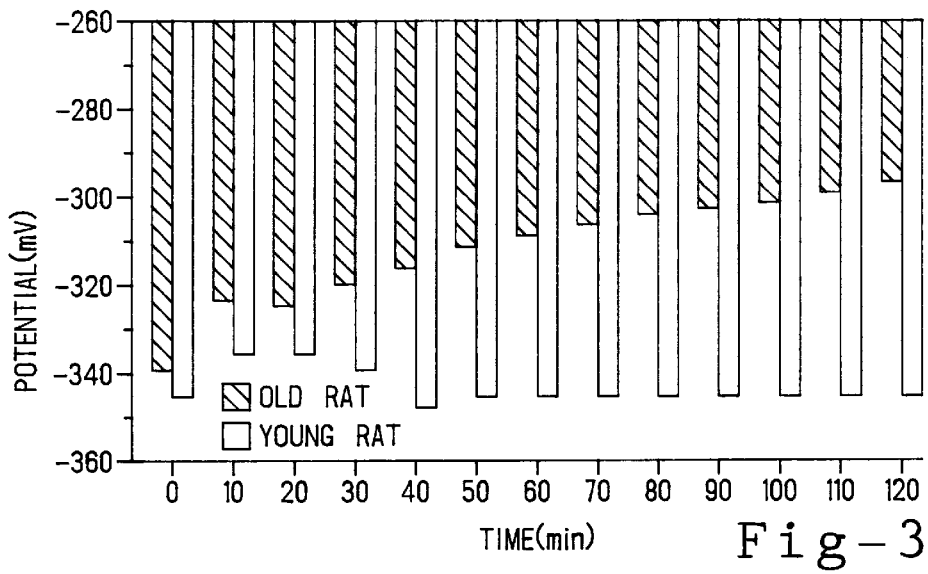
FIG. 3: The changes in potential (E) of a solution of $I^-/I_2$ with time on the skin of old rats.

2. Experiments and Results (a) Determination of "Peroxide Number" (ROOH) on Rat Skin FIGS. 2 and 3 show the changes in the potential (E) of the iodide solution in time. The experiment was carried out using young rats (100 g) (n=10) (FIG. 2) and old rats (400 g) (FIG. 3). The results indicate that the potential of the tested solution did not change with time on the skin of the young rats while a significant change was detected on the skin of the old rats. It can be concluded that the concentration of ROOH in the skin of young rats is very low while the concentration of ROOH on the skin of old rats is higher. These results are in correlation with the free radical theory of aging which suggests that the oxidation of animal tissue increases with age. The production of iodine from the iodide solution was validated by titration of the $I_2$ with a solution of thiosulfate.

(b) Determination of "Peroxide Number" (ROOH) in Irradiated Young Rats

Figure 4:
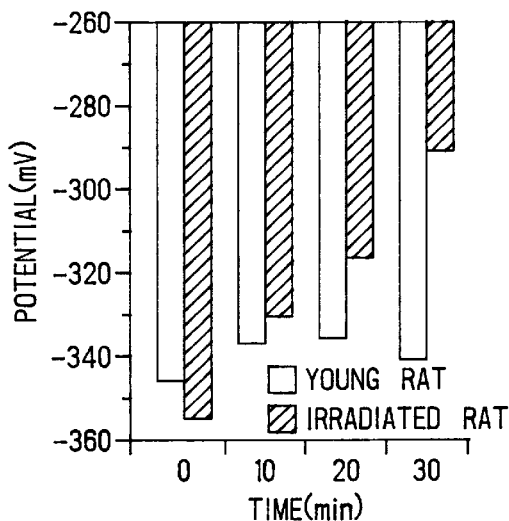
FIG. 4: The changes in potential (E) on skin of irradiated young rats and in a control group.

Young rats (n=10) were exposed to τ-irradiation (950 rads). Three hours following the irradiation the peroxide number of the irradiated skin was determined as described by following the changes in the potentials (E) of the tested solution. The increase in the potential indicates the production of iodine from ROOH (Reaction 1). FIG. 4 shows that following irradiation a significant change in the potential (E) occurred as compared to untreated rats of the same age thereby indicating an increase in the production of iodine (increase in the concentration of ROOH in the skin). It can be seen that in rats following 30 minutes of exposure to the tested solution, the potential recorded in the irradiated young rats was similar to the potential recorded in the unirradiated old rats indicating similar concentration of ROOH.

Oxidative stress such as τ-irradiation is known to initiate lipid peroxidation in animal and human tissue as shown in the past. The results obtained by the present non-invasive measurement of the skin support this hypothesis.

(c) Induction of Oxidative Stress on Rat Skin by the Azo Compound AAPH

Figure 5:
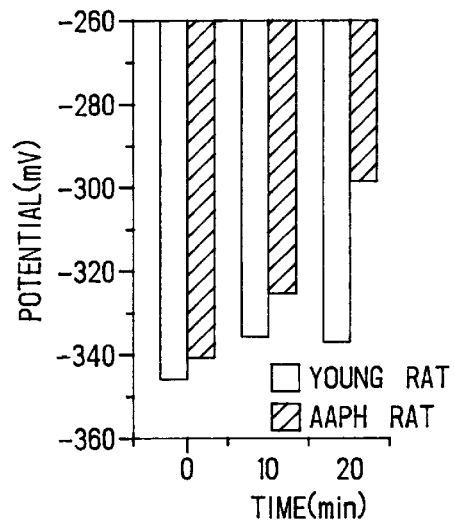
FIG. 5: The changes in the potential (E) on skin of young rats treated with a 100 mM solution of AAPH for 24 hours as compared to a control group.

Lipid peroxidation is often initiated by the use of the peroxy radical initiator AAPH (2-aminopropanedihydroxychloride) [Niki, E., et al., Bull. Chem. Soc. Jpn. 59: 497–501 (1986)]. It has been shown in the past that these compounds can produce a flux of peroxy radicals which in turn can initiate lipid peroxidation. The employment of pad soaked with a 100 mM AAPH solution to rat skin for 24 hours resulted in a significant increase in the "peroxide number" of the skin (increase in ROOH in the skin). This was determined by the increase in the potential (E) of the tested solution $I_2/I^-$ indicating the production of $I_2$ from $I^-$ (Reaction 1). FIG. 5 shows that 24 hours following the treatment with AAPH an increase in the ROOH occurred. Twenty seven minutes after the introduction of the $_2/I^-$ solution the potential increased from −360 mV to −296 mv indicating an increase in $I_2$ concentration.

Figure 6:
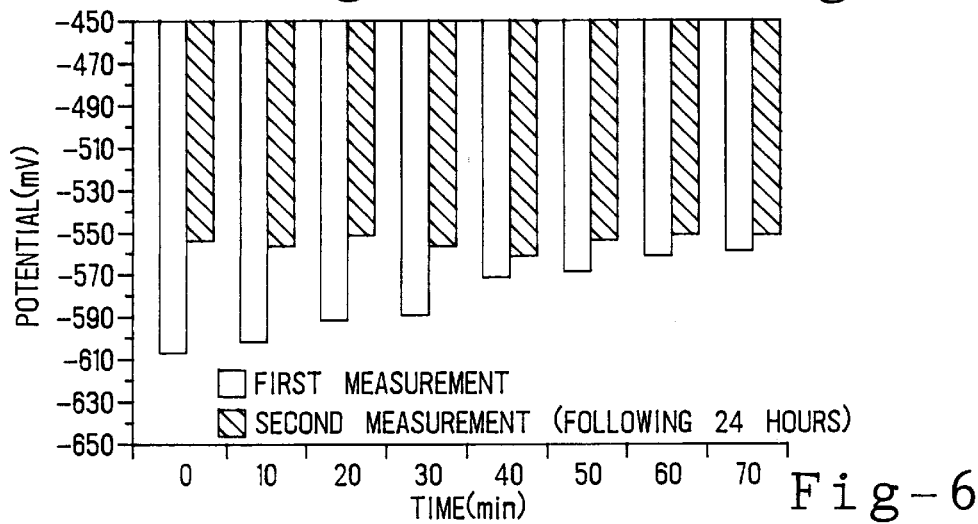
FIG. 6: Changes in the potential (E) of a Fe(III)/Fe(II) on skin of young rats.

(d) Determination of Antioxidant Activity by the Noninvasive Measurement of a Solution of Fe(III) on Rat Skin The antioxidant activity of rat skin was determined by the employment of a solution of 0.2M $FeCl_3$ in a 50 mM KCl buffer pH$\leq$2. As a result of the interaction between reducing equivalents in the skin and the oxidized form of iron, an electrochemical cell is produced (Fe(III)/ Fe(II)). The iron (III) is reduced to iron (II) by reducing equivalents present on surface of the skin and in the epidermis. The reducing equivalents are in correlation with the antioxidant activity as previously shown [Kohen, R., et al., ibid.] and as validated by measuring the antioxidant activity by conventional methods. FIG. 6 shows the changes in the potential of the Fe(III)/Fe(II) solution indicating the reducing power (antioxidant power) of the skin. Measurement of the skin reducing power 24 hours following the first measurements revealed that no Fe(II) was produced thereby indicating that no reducing equivalents were present in the skin.

We claim:

1. A non-invasive device for the quantitative determination of the level of oxidants and/or antioxidants in the skin of a subject comprising:

a pair of a reference electrode and a working electrode which are connected to electrical voltage measuring means;

a test solution container which is open at a bottom side thereof which is placed on the skin of said subject and is releasably but sealingly affixed to the skin by suitable means, filled with said test solution and permitting contact between said test solution and the skin, and is open at a top side thereof through which said electrodes are immersed in said test solution.

2. A device according to claim 1 further comprising means accommodating said electrodes and holding the same within said test solution.

3. A device according to claim 1 wherein said reference electrode is Ag/AgCl or a calomel electrode and said working electrode is a glossy carbon, gold or platinum electrode.

4. A device according to claim 1 wherein said container is made from plastics material.

5. A device according to claim 1 wherein said container is an open-sided hollow cylinder.

6. A device according to claim 4 wherein said container is made from Plexyglass®.

7. A device according to claim 1 wherein said means for affixing said test solution container to the skin of the subject are silicone glue.

8. A device for the quantitative determination of the level of oxidants in the skin according to claim 1 wherein said test solution is an aqueous iodide or iodide-iodine.

9. A device according to claim 8 wherein said test solution is an aqueous $KI/I_2$ solution.

10. A device according to claim 8 for quantitatively measuring the lipid hydroperoxide level in the skin.

11. A device for the quantitative determination of the level of antioxidants in the skin according to claim 1 wherein said test solution is an acidic aqueous Fe(III) salt solution.

12. A device according to claim 11 wherein said Fe(III) salt is $FeCl_3$, $FeNH_4(SO_4)_2$ or $Fe(SO_4)_2$.

13. A device for the quantitative determination of the level of antioxidants in the skin according to claim 1 wherein said test solution is an aqueous iodine or Fe(III) chelate solution.

14. A device according to claim 1 further comprising electrical voltage recording means.

15. A non-invasive method for the quantitative determination of the level of oxidants or antioxidants in the skin of a subject comprising the steps of:

sealingly affixing to the skin of the subject a test solution container which is open at the side thereof which is placed on the skin of said subject in a releasable manner by suitable means;

filling said container with a suitable test solution, said test solution containing reagents which are capable of being oxidized or reduced by oxidants or antioxidants present in the skin of said subject, respectively;

immersing a pair of a reference electrode and a working electrode, which are connected to electrical voltage measuring means, in said test solution; and measuring the electrical voltage of said test solution at appropriate time points;

whereby the concentration of the oxidants or antioxidants in the skin of said subject is determined from the change in the electric potential of said test solution.

16. A method according to claim 15 wherein said container is equipped with means for accommodating said electrodes and holding the same within said test solution.

17. A method according to claim 15 wherein said reference electrode is Ag/AgCl or a calomel electrode and said working electrode is a glossy carbon, gold or platinum electrode.

18. A method according to claim 15 wherein said container is made from plastics material.

19. A method according to claim 15 wherein said container is an open-sided hollow cylinder.

20. A method according to claim 18 wherein said container is made from Plexyglass®.

21. A method according to claim 15 wherein said means for affixing said test solution container to the skin of the subject are silicone glue.

22. A method according to claim 15 for the quantitative determination of the level of oxidants in the skin wherein said test solution is an aqueous iodide or iodide-iodine.

23. A method according to claim 22 wherein said test solution is an aqueous $KI/I_2$ solution.

24. A method according to claim 23 for quantitatively measuring the lipid hydroperoxide level in the skin.

25. A method according to claim 15 for the quantitative determination of the level of antioxidants in the skin wherein said test solution is an acidic aqueous Fe(III) salt solution.

26. A method according to claim 25 wherein said Fe(III) salt is $FeCl_3$, $FeNH_4(SO_4)_2$ or $Fe(SO_4)_2$.

27. A method according to claim 15 for the quantitative determination of the level of antioxidants in the skin wherein said test solution is an aqueous iodine or Fe(III) chelate solution.

28. A method of evaluating damage to skin of a subject following exposure to UV or radioactive radiation, burns, inflammation or ischemia by determining decrease of level of antioxidants in the skin of said subject by the method according to claim 15.

29. A method of evaluating damage to skin of a subject following exposure to UV or radioactive radiation, burns, inflammation or ischemia by determining increase of level of oxidants in the skin of said subject by the method according to claim 15.

* * * * *